United States Patent [19]
Winterhalter et al.

[11] Patent Number: 5,972,663
[45] Date of Patent: Oct. 26, 1999

[54] MICROORGANISMS AND PROCESSES FOR THE FERMENTATIVE PREPARATION OF L-CYSTEINE, L-CYSTINE, N-ACETYLSERINE OR THIAZOLIDINE DERIVATIVES

[75] Inventors: Christoph Winterhalter, Pöcking; Walfred Leinfelder, München, both of Germany

[73] Assignee: Consortium für Elektrochemische Industrie GmbH, Munich, Germany

[21] Appl. No.: 09/097,759

[22] Filed: Jun. 16, 1998

[30] Foreign Application Priority Data

Jun. 19, 1997 [DE] Germany ............... 197 26 083

[51] Int. Cl.⁶ ............... C12P 13/12; C12N 1/20; C12N 15/31; C12N 15/67
[52] U.S. Cl. ............... 435/113; 435/69.1; 435/252.31; 435/252.32; 435/252.33; 435/252.35; 435/320.1; 530/324; 536/23.1; 536/23.7
[58] Field of Search ............... 435/252.3, 320.1, 435/69.1, 113, 252.31, 252.32, 252.33, 252.35; 530/324; 536/23.7, 23.1

[56] References Cited

FOREIGN PATENT DOCUMENTS

| | | |
|---|---|---|
| 0101052 | 2/1984 | European Pat. Off. . |
| 19539952 | 4/1997 | Germany . |
| 19548222 | 6/1997 | Germany . |
| WO/97/15673 | 5/1997 | WIPO . |

OTHER PUBLICATIONS

Gambino et al., J. Bacteriology 175(10):2888–2894 (1993).
Ishida et al., Antimicrobial Agents and Chemotherapy 39(2):453–457 (1995).
Ronald C. Simpson et al., Biochimica et Biophysic Acta, 496 (1977), 12–19.
Kredich et al. in J. of Biol. Chem. 248, 17: 6187–6196.
Ok Hee Ryu et al., Biotechnology Lettes 17 No. 3, 275–280 (Mar. 1995).
S.P. Cohen et al., Journal of Bacteriology, Mar. 1993, 175: 5, 1484–1492.
P.F. Miller and M.C. Sulavik, Molecular Microbiology (1996) 21(3), 441–448.
T. Köhler et al., Molecular Microbiology (1997) 23(2), 345–354.
A.A Neyfakh et al., Proc. Natl. Acad. Sci. USA 88: 4781–4785 (1991).
J.M. Tennent et al., J. Gen. Microbiol. 135: 1–10 (1989).
Gaitonde, M.K. (1967), Biochem. J. 104, 627–633.
Sang–Han Lee et al., Biochemical and Biophysical Research Communications, vol. 213, No. 3 (1995), pp. 837ff.
Saiki et al. 1988, Science 239: 487–491.
Ausubel et al., 1987, 2.4.1–2.4.2, Current Protocols in Molecular Biology, Greene Publishing Associates and Wiley–Interscience.
M.P. Schubert, J. Biol. Chem. 121, 539–548 (1937).
Nilsen I et al: "Isolation of cmr, a novel *Escherichia coli* chloramphenicol resistance gene encoding a putative eflux pump", J. Bacteriol, Bd. 178, No. 11, Jun. 1996, pp. 3188–3193.
E.M.B.L. Databases, Dec. 21, 1996, Mori H: "*E. coli* genomic DNA", Nukleotiden 2834—3754.
Vrljic M et al: "A new type of transport with a new typr of cellular function: l–lysine export from corynebacterium glutamicum", Molecular Microbiology, Bd. 22, No. 5, Dec. 1996, pp. 815–826.
Derwent Abstract (97–333867 [31]) corresponding to DE 195 48 222 A1.
Paulsen I et al: "Proton–dependent multidrug efflux systems", Microbiological Reviews, Bd. 60, Dec. 1996, pp. 575–608.

*Primary Examiner*—Johnny F. Railey, II
*Attorney, Agent, or Firm*—Collard & Roe, P.C.

[57] ABSTRACT

Microorganisms and processes for the fermentative preparation of L-cysteine, L-cystine, N-acetylserine or thiazolidine derivatives. The microorganism strain which is suitable for the fermentative preparation of L-cysteine, L-cystine, N-acetylserine and/or thiazolidine derivatives, overexpresses at least one gene which encodes a protein which is directly suitable for secreting antibiotics, or other substances which are toxic for the microorganism, out of the cell.

14 Claims, 9 Drawing Sheets cysE-fw: (SEQ. ID. NO: 5)

5'-TGG ACC A<u>GA GCT C</u>TG GCT GGC GCA TCG CTT CGG CGT TG-3'
         SacI

FIG. 6 cysE-rev: (SEQ. ID. NO: 6)

5'-CTC G<u>AT GCA T</u>TA CGT AGG GGT ATC CGG GAG CGG TAT TG-3'
       NsiI

FIG. 7 mar-fw: (SEQ. ID. NO: 7)

5'-TTT GGC GCG CCG ATC AGC GGC GGC GCA ACC ATC AG-3'
         AscI

FIG. 8 mar-rev: (SEQ. ID. NO: 8)

5'-GCC TTA ATT AAG ATC GAC ACT CAG GCT GTA CTG GCG AC-3'
         PacI

FIG. 9

ORF306-fw: (SEQ. ID. NO: 9)

5'-GGA ATT CAT TAA TCC GGC GAC TAA CGA ATC AAC TG-3'.
           AsnI

FIG. 10

ORF306-rev: (SEQ. ID. NO: 10)

5'-GCC TTA ATT AAC GCT ATG TAG TTT GTT CTG GCC CCG-3'
       PacI

FIG. 11

GAPDH-fw (SEQ. ID. NO: 11)

5'-GTC GAC GCG TGA GGC GAG TCA GTC GCG TAA TGC-3'

MluI

FIG. 12

GAPDH-rev: (SEQ. ID. NO: 12)

5'-GAC CTT AAT TAA GAT CTC ATA TGT TCC ACC AGC TAT TTG TTA G-3'

PacI        NdeI

FIG. 13

SEQUENCE LISTING

<160> NUMBER OF SEQ ID NOS: 12

<210> SEQ ID NO 1
<211> LENGTH: 43
<212> TYPE: PRT
<213> ORGANISM: Escherichia coli

<400> SEQUENCE: 1

Met Ser Arg Lys Asp Gly Val Leu Ala Leu Val Val Val Trp
 1               5                  10                  15

Gly Leu Asn Phe Val Val Ile Lys Val Gly Leu His Asn Met Pro Arg
            20                  25                  30

Leu Met Leu Ala Gly Leu Arg Phe Met Leu Val
        35                  40

<210> SEQ ID NO 2
<211> LENGTH: 306
<212> TYPE: PRT
<213> ORGANISM: Escherichia coli

<400> SEQUENCE: 2

Met Lys Phe Arg Gly Gly Arg Met Ser Arg Lys Asp Gly Val Leu Ala
 1               5                  10                  15

Leu Leu Val Val Val Trp Gly Leu Asn Phe Val Val Ile Lys Val
            20                  25                  30

Gly Leu His Asn Met Pro Arg Leu Met Leu Ala Gly Leu Arg Phe Met
        35                  40                  45

Leu Val Ala Phe Pro Ala Ile Phe Phe Val Ala Arg Pro Lys Val Pro
    50                  55                  60

Leu Asn Leu Leu Leu Gly Tyr Gly Leu Thr Ile Ser Phe Ala Gln Phe
65                  70                  75                  80

Ala Phe Leu Phe Cys Ala Ile Asn Phe Gly Met Pro Ala Gly Leu Ala
                85                  90                  95

Ser Leu Val Leu Gln Ala Gln Ala Phe Phe Thr Ile Met Leu Gly Ala
            100                 105                 110

Phe Thr Phe Gly Glu Arg Leu His Gly Lys Gln Leu Ala Gly Ile Ala
        115                 120                 125

Leu Ala Ile Phe Gly Val Leu Val Leu Ile Glu Asp Ser Leu Asn Gly
    130                 135                 140

Gln His Val Ala Met Leu Gly Phe Met Leu Thr Leu Ala Ala Ala Phe
145                 150                 155                 160

Ser Trp Ala Cys Gly Asn Ile Phe Asn Lys Lys Ile Met Ser His Ser
                165                 170                 175

Thr Arg Pro Ala Val Met Ser Leu Val Ile Trp Ser Ala Leu Ile Pro
            180                 185                 190

Ile Ile Pro Phe Phe Val Ala Ser Leu Ile Leu Asp Gly Ser Ala Thr
        195                 200                 205

Met Ile His Ser Leu Val Thr Ile Asp Met Thr Thr Ile Leu Ser Leu
    210                 215                 220

Met Tyr Leu Ala Phe Val Ala Thr Ile Val Gly Tyr Gly Ile Trp Gly
225                 230                 235                 240

Thr Leu Leu Gly Arg Tyr Glu Thr Trp Arg Val Ala Pro Leu Ser Leu
                245                 250                 255

Leu Val Pro Val Val Gly Leu Ala Ser Ala Ala Leu Leu Leu Asp Glu
            260                 265                 270

Arg Leu Thr Gly Leu Gln Phe Leu Gly Ala Val Leu Ile Met Thr Gly
                275                 280                 285

Leu Tyr Ile Asn Val Phe Gly Leu Arg Trp Arg Lys Ala Val Lys Val
        290                 295                 300

Gly Ser
305

<210> SEQ ID NO 3
<211> LENGTH: 299
<212> TYPE: PRT
<213> ORGANISM: Escherichia coli

<400> SEQUENCE: 3

Met Ser Arg Lys Asp Gly Val Leu Ala Leu Val Val Val Val Trp
 1               5                  10                  15

Gly Leu Asn Phe Val Ile Lys Val Gly Leu His Asn Met Pro Arg
            20                  25                  30

Leu Met Leu Ala Gly Leu Arg Phe Met Leu Val Ala Phe Pro Ala Ile
            35                  40                  45

Phe Phe Val Ala Arg Pro Lys Val Pro Leu Asn Leu Leu Gly Tyr
        50                  55                  60

Gly Leu Thr Ile Ser Phe Ala Gln Phe Ala Phe Leu Phe Cys Ala Ile
65                  70                  75                  80

Asn Phe Gly Met Pro Ala Gly Leu Ala Ser Leu Val Leu Gln Ala Gln
                85                  90                  95

Ala Phe Phe Thr Ile Met Leu Gly Ala Phe Thr Phe Gly Glu Arg Leu
            100                 105                 110

His Gly Lys Gln Leu Ala Gly Ile Ala Leu Ala Ile Phe Gly Val Leu
        115                 120                 125

Val Leu Ile Glu Asp Ser Leu Asn Gly Gln His Val Ala Met Leu Gly
130                 135                 140

Phe Met Leu Thr Leu Ala Ala Ala Phe Ser Trp Ala Cys Gly Asn Ile
145                 150                 155                 160

Phe Asn Lys Lys Ile Met Ser His Ser Thr Arg Pro Ala Val Met Ser
                165                 170                 175

Leu Val Ile Trp Ser Ala Leu Ile Pro Ile Ile Pro Phe Phe Val Ala
            180                 185                 190

Ser Leu Ile Leu Asp Gly Ser Ala Thr Met Ile His Ser Leu Val Thr
        195                 200                 205

Ile Asp Met Thr Thr Ile Leu Ser Leu Met Tyr Leu Ala Phe Val Ala
210                 215                 220

Thr Ile Val Gly Tyr Gly Ile Trp Gly Thr Leu Leu Gly Arg Tyr Glu
225                 230                 235                 240

Thr Trp Arg Val Ala Pro Leu Ser Leu Val Pro Val Val Gly Leu
                245                 250                 255

Ala Ser Ala Ala Leu Leu Leu Asp Glu Arg Leu Thr Gly Leu Gln Phe
            260                 265                 270

Leu Gly Ala Val Leu Ile Met Thr Gly Leu Tyr Ile Asn Val Phe Gly
        275                 280                 285

Leu Arg Trp Arg Lys Ala Val Lys Val Gly Ser
        290                 295

<210> SEQ ID NO 4
<211> LENGTH: 266
<212> TYPE: PRT
<213> ORGANISM: Escherichia coli

<400> SEQUENCE: 4

```
Met Leu Ala Gly Leu Arg Phe Met Leu Val Ala Phe Pro Ala Ile Phe
  1               5                  10                  15

Phe Val Ala Arg Pro Lys Val Pro Leu Asn Leu Leu Leu Gly Tyr Gly
             20                  25                  30

Leu Thr Ile Ser Phe Ala Gln Phe Ala Phe Leu Phe Cys Ala Ile Asn
         35                  40                  45

Phe Gly Met Pro Ala Gly Leu Ala Ser Leu Val Leu Gln Ala Gln Ala
     50                  55                  60

Phe Phe Thr Ile Met Leu Gly Ala Phe Thr Phe Gly Glu Arg Leu His
 65                  70                  75                  80

Gly Lys Gln Leu Ala Gly Ile Ala Leu Ala Ile Phe Gly Val Leu Val
             85                  90                  95

Leu Ile Glu Asp Ser Leu Asn Gly Gln His Val Ala Met Leu Gly Phe
        100                 105                 110

Met Leu Thr Leu Ala Ala Ala Phe Ser Trp Ala Cys Gly Asn Ile Phe
    115                 120                 125

Asn Lys Lys Ile Met Ser His Ser Thr Arg Pro Ala Val Met Ser Leu
130                 135                 140

Val Ile Trp Ser Ala Leu Ile Pro Ile Pro Phe Phe Val Ala Ser
145                 150                 155                 160

Leu Ile Leu Asp Gly Ser Ala Thr Met Ile His Ser Leu Val Thr Ile
            165                 170                 175

Asp Met Thr Thr Ile Leu Ser Leu Met Tyr Leu Ala Phe Val Ala Thr
            180                 185                 190

Ile Val Gly Tyr Gly Ile Trp Gly Thr Leu Leu Gly Arg Tyr Glu Thr
        195                 200                 205

Trp Arg Val Ala Pro Leu Ser Leu Leu Val Pro Val Val Gly Leu Ala
210                 215                 220

Ser Ala Ala Leu Leu Leu Asp Glu Arg Leu Thr Gly Leu Gln Phe Leu
225                 230                 235                 240

Gly Ala Val Leu Ile Met Thr Gly Leu Tyr Ile Asn Val Phe Gly Leu
            245                 250                 255

Arg Trp Arg Lys Ala Val Lys Val Gly Ser
        260                 265
```

<210> SEQ ID NO 5
<211> LENGTH: 38
<212> TYPE: DNA
<213> ORGANISM: Escherichia coli

<400> SEQUENCE: 5
tggaccagag ctctggctgg cgcatcgctt cggcgttg                         38

<210> SEQ ID NO 6
<211> LENGTH: 38
<212> TYPE: DNA
<213> ORGANISM: Escherichia coli

<400> SEQUENCE: 6
ctcgatgcat tacgtagggg tatccgggag cggtattg                         38

<210> SEQ ID NO 7
<211> LENGTH: 35
<212> TYPE: DNA
<213> ORGANISM: Escherichia coli

<400> SEQUENCE: 7

```
tttggcgcgc cgatcagcgg cggcgcaacc atcag                              35

<210> SEQ ID NO 8
<211> LENGTH: 38
<212> TYPE: DNA
<213> ORGANISM: Escherichia coli

<400> SEQUENCE: 8
gccttaatta agatcgacac tcaggctgta ctggcgac                           38

<210> SEQ ID NO 9
<211> LENGTH: 35
<212> TYPE: DNA
<213> ORGANISM: Escherichia coli

<400> SEQUENCE: 9
ggaattcatt aatccggcga ctaacgaatc aactg                              35

<210> SEQ ID NO 10
<211> LENGTH: 36
<212> TYPE: DNA
<213> ORGANISM: Escherichia coli

<400> SEQUENCE: 10
gccttaatta acgctatgta gtttgttctg gccccg                             36

<210> SEQ ID NO 11
<211> LENGTH: 33
<212> TYPE: DNA
<213> ORGANISM: Escherichia coli

<400> SEQUENCE: 11
gtcgacgcgt gaggcgagtc agtcgcgtaa tgc                                33

<210> SEQ ID NO 12
<211> LENGTH: 43
<212> TYPE: DNA
<213> ORGANISM: Escherichia coli

<400> SEQUENCE: 12
gaccttaatt aagatctcat atgttccacc agctatttgt tag                     43
```

MICROORGANISMS AND PROCESSES FOR THE FERMENTATIVE PREPARATION OF L-CYSTEINE, L-CYSTINE, N-ACETYLSERINE OR THIAZOLIDINE DERIVATIVES

BACKGROUND OF THE INVENTION

1. Field of the Invention

The invention relates to microorganisms and processes for the fermentative preparation of L-cysteine, L-cystine, N-acetylserine or thiazolidine derivatives.

2. The Prior Art

It is well known to prepare many amino acids by fermentation. However, there has previously not been any economical process for the fermentative preparation of L-cysteine.

Thiazolidine derivatives and the corresponding hemithioketals are generally produced when cysteine is condensed with ketones or aldehydes. The chemical condensation of cysteine with different ketones or aldehydes, in particular with α-ketoacids, is known. The condensation takes place with the hemithioketal as the intermediate. The hemithioketal is produced by the nucleophilic attack of the free electron pair of the sulfur on the electron-deficient carbon atom of the aldehyde group or keto group. Ring closure with the elimination of water then leads to the corresponding thiazolidine derivative.

The formation of thiazolidine derivatives is shown in a general manner in the following reaction sequence.

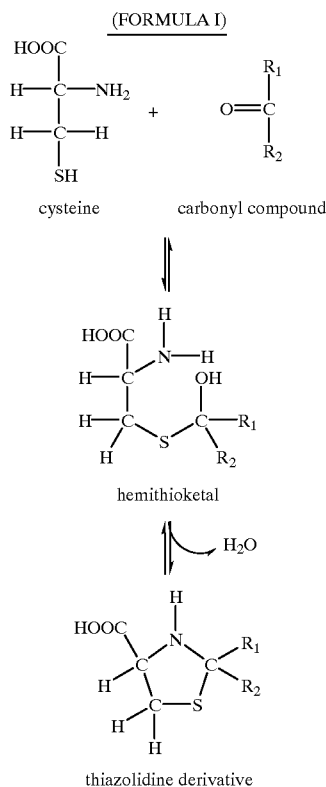

In this reaction, $R_1$ and $R_2$ can denote any organic radicals.

The starting compounds are consequently in equilibrium with the thiazolidine derivative through the intermediate hemithioketal. For this reason, the hemithioketal is generally also present in aqueous solution in addition to the thiazolidine derivative.

According to the present invention, "thiazolidine derivative" is also understood as meaning an equilibrium of these substances with the corresponding intermediate hemithioketal.

It has not previously been reported that thiazolidines are direct metabolites of cells. All reports of the formation of thiazolidines by cells are based on the external addition, in an excess, of one of the starting compounds, usually L-cysteine. This cysteine is then converted into pyruvate by desulfhydration and deamination. The pyruvate is then reacted with the added cysteine. (Ronald C. Simpson et al., Biochimica et Biophysic Acta, 496 (1977), 12–19). Kredich et al. have reported, in J. of Biol. Chem. 248, 17: 6187–6196, that 2-methyl-2,4-thiazolidinedicarboxylic acid is formed in vitro when L-cysteine is subjected to an enzymic desulfhydration. These authors consider that it is extremely unlikely that this substance is formed in vivo.

It is known to use thiazolidines as racemic precursors for preparing L-cysteine by means of biotransformation (EP-A 0 101 052, Ok Hee Ryu et al., Biotechnology Letters 17 No. 3, 275–280 (March 1995)). When the racemate is employed for preparing L-cysteine, it has to be converted stereoselectively into L-cysteine using enzymes or whole cells. The remaining diastereomers have to then be racemized once again. For these reasons, this biotransformation has a high cost.

The chemical synthesis of thiazolidines from racemic cysteine and a corresponding ketone or aldehyde leads to four different diastereomers. Carrying out a chemical synthesis from enantiomerically pure L-cysteine is expensive. There are difficulties in subsequently isolating the L-cysteine. For this reason, a process for preparing thiazolidine diastereomers which possess the R configuration at the C4 atom suffers from the high costs of the starting compounds.

SUMMARY OF THE INVENTION

The present invention relates to microorganisms which are suitable for fermentatively preparing L-cysteine, L-cystine, N-acetylserine and/or thiazolidine derivatives.

A microorganism strain according to the invention is one that overexpresses at least one gene which encodes a protein which is directly suitable for secreting antibiotics, or other substances which are toxic for the organism, out of the cell.

Within the meaning of the invention, substances which are toxic for the organism are to be understood as preferably being compounds which exert a negative effect on the growth of the organism. Examples of such compounds are carboxylic acids or carboxylic acid derivatives which are present at high intracellular concentrations.

In addition, genes which encode proteins which are directly suitable for secreting antibiotics and other toxic substances out of the cell are termed efflux genes. Also genes which lead to the formation of such proteins are termed efflux genes.

The invention consequently relates to the use of efflux genes for the purpose of augmenting the expression, in fermentation, of amino acids or of amino acid derivatives which are formed intracellularly.

At least one gene can be selected from the group consisting of mar locus (S. P. Cohen et al., Journal of Bacteriology, March 1993, 175 (5), 1484–1492), emr locus, acr locus, cmr locus (see P. F. Miller and M. C. Sulavik, Molecular Microbiology (1996) 21 (3), 441–448), mex genes (T. Köhler et al., Molecular Microbiology (1997)

23(2), 345–354), bmr gene (A. A. Neyfakh et al., Proc. Natl. Acad. Sci. USA 88: 4781–4785 (1991)) and qacA gene (J. M. Tennent et al., J. Gen. Microbiol. 135: 1–10 (1989). This gene is preferably overexpressed as an efflux gene in the microorganism according to the invention. The genes of the mar locus are preferably overexpressed, as efflux genes, in the microorganism according to the invention.

A gene encoding a protein which comprises the amino acid sequence of (SEQ ID NO: 1), or an amino acid sequence which has greater than 50% sequence homology with (SEQ ID NO: 1), is particularly preferably overexpressed in the microorganism according to the invention.

Preference is given to the sequence homology with (SEQ ID NO: 1) being greater than 75%, and particular preference is given to the sequence homology with (SEQ ID NO: 1) being greater than 90%.

The invention consequently also relates to genes encoding a protein which comprises the amino acid sequence of (SEQ ID NO: 1), or an amino acid sequence which has greater than 50% sequence homology with (SEQ ID NO: 1).

The invention furthermore relates to proteins which comprise the amino acid sequence of (SEQ ID NO: 1) or an amino acid sequence which has greater than 50% sequence homology with (SEQ ID NO: 1).

Preference is given to the sequence homology with (SEQ. ID NO: 1) being greater than 75%, and particular preference is given to the sequence homology with (SEQ ID NO: 1) being greater than 90%.

For example, proteins according to the invention can possess the following amino acid sequence of (SEQ ID NO: 2).

In the following, the open reading frame which encodes the protein having the amino acid sequence depicted in SEQ ID NO: 2 is also termed ORF 306.

The following amino acid sequence of (SEQ ID NO: 3) represents another example of a protein according to the invention.

Those proteins which possess an amino acid sequence which has greater than 50% sequence homology, at the amino acid level, with the amino acid sequence depicted in (SEQ ID NO: 2) or (SEQ ID NO: 3) are also proteins according to the invention.

Preference is given to the sequence homology of the proteins according to the invention with (SEQ ID NO: 2) or (SEQ ID NO: 3) being greater than 75%, and particular preference is given to the sequence homology with (SEQ ID NO: 2) or (SEQ ID NO: 3) being greater than 90%.

Those genes which encode proteins which possess an amino acid sequence as depicted in (SEQ ID NO: 2) or (SEQ ID NO: 3) are according to the invention. Also, an amino acid sequence which has greater than 50%, preferably 75%, particularly preferably 90%, sequence homology, at the amino acid level, with the amino acid sequence depicted in (SEQ ID NO: 2) or (SEQ ID NO: 3), are therefore genes according to the invention.

All the homology values which are mentioned for the present invention relate to results which are obtained using the "Wisconsin Package Version 9.0, Genetics Computer Group (GCG), Madison, Wis." computer program. The homology is determined by searching in the database using the "fasta" subprogram and the default values (word size 2). The sequences having the greatest similarity are then examined for homology using the "gap" subprogram and the "gap creation penalty 12" and "gap extension penalty 4" default parameters.

Another example of the overexpression of a gene according to the invention for the purpose of increasing cysteine formation is the overexpression of a 5.5 kb DNA fragment which also encodes the mar locus. This plasmid, which is designated 100-1-1, was deposited, as E. coli K12 W3110, in the DSMZ Deutsche Sammlung von Mikroorganismen und Zellkulturen (German Collection of Microorganisms and Cell Cultures) GmbH, D-38124 Braunschweig, Germany, under the number DSM 11545. FIG. 1 shows a map of the plasmid 100-1-1 which can be used for amplifying genes according to the invention by means of PCR.

Known methods may be used for gene modification. For example the technique of site-directed mutagenesis may be used to achieve further specific modification of these genes. This modification occurs at the desired position in the sequence. Consequently, microorganisms which contain genes which have been modified in this manner are also in accordance with the invention. That is as long as the genes which have been modified in this way contribute to the preparation of L-cysteine, L-cystine, N-acetylserine and/or thiazolidine derivatives.

Within the meaning of the invention, overexpression is to be understood as indicating that the protein is expressed at least twice as strongly in the microorganism according to the invention as in the wild-type organism from which the protein originates.

The protein is preferably expressed at least five times as strongly in the microorganism according to the invention as in the wild-type organism, particularly preferably at least ten times as strongly as in the wild-type organism from which the protein originates.

As compared to the starting strain, no clear increase in the yield of L-cysteine or thiazolidine derivatives can be observed without overexpression of these genes. Overexpression can be for example by means of independent transcription using a separate promotor, or, for example, without the gene encoding marA being present in many copies on a plasmid.

The increase in yield resulting from the over-expression of the sequences was all the more unexpected and surprising. This is because overexpression of the gene product, which is described in the literature, of the open reading frame ORF266, whose sequence, from the methionine in position 41 in (SEQ ID NO: 2) onwards, corresponds to sequence (SEQ ID NO: 4). This does not lead to an increase in the yield of L-cysteine.

There is a number of known methods for achieving overexpression of a gene. One possibility is, for example, to express the gene on a plasmid which is present in the cell at a high copy number. Such plasmids are known. Examples of these plasmids include pACYC177, pACYC184, derivatives of pACYC184, pBR322, other pBR derivatives, pBluescript, pUC18, pUC19 and other plasmids which are conventionally used in Escherichia coli.

Plasmids which are preferred for the overexpression according to the invention are pACYC177, pACYC184, derivatives of pACYC184, pBR322 and other pBR derivatives.

Particular preference is given to pACYC184 and its derivatives such as pACYC184-LH (deposited in the DSMZ Deutsche Sammlung von Mikroorganismen und Zellkulturen GmbH, D-38124 Braunschweig under the number DSM 10172).

The invention consequently also relates to plasmids which contain genes according to the invention.

One possibility for augmenting expression is to increase the copy number of an efflux gene by means of amplifying the gene segment in the chromosome. Another possibility is to use strong promoters in order to improve transcription of the efflux gene.

Examples of suitable strong promoters are the GAPDH promoter, the tac promoter ($p_{tac}$), the Lac promoter ($p_{Lac}$) the trp promoter ($p_{trp}$), lambda PL or lambda PR. The GAPDH promoter or the tac promoter ($p_{tac}$) is preferred. The GAPDH promoter is particularly preferred.

A further possibility for augmenting expression is to inactivate repressor genes which exert an inhibitory effect on the expression of an efflux gene. In the case of the mar gene locus, this would, for example, involve inactivation of the mar R gene.

Elements which exert a positive effect on translation also contribute to overexpression of the efflux gene. Examples of such elements are a good ribosome-binding site (e.g. Shine-Dalgarno sequence) or a downstream box. The good ribosome-binding site of the GAPDH gene is a preferred element which exerts a positive effect on translation.

In order to be expressed, the efflux genes are transformed into a microorganism which produces L-cysteine. Efflux genes are preferably transformed into microorganisms which are selected from the group Bacillus, such as *B. subtilis*, Corynebacterium, such as *C. glutamicum*, Streptomyces and *E. coli*.

The efflux genes are preferably transformed into organisms whose cysteine metabolism is deregulated. This means that the formation of increased quantities of L-cysteine and, possibly, the subsequent formation of a thiazolidine derivative of L-cysteine or of N-acetylserine occurs.

Examples of microorganisms which produce increased quantities of L-cysteine are microorganisms which possess a feedback-resistant CysE allele.

In another preferred embodiment, microorganisms which form a thiazolidine derivative intracellularly by means of the condensation of L-cysteine and a ketone or aldehyde, in particular pyruvate, are transformed.

Microorganisms which produce increased quantities of L-cysteine are described, for example, in patent application DE 19539952. (DE 19539952 is incorporated by reference).

A person skilled in the art is familiar, for example from standard textbooks, with methods for transforming a microorganism. All the known methods can be used for producing a microorganism according to the invention.

Augmented expression of the efflux genes in microorganisms can produce amino acids or amino acid derivatives which are formed intracellularly, such as L-cysteine, L-cystine, N-acetylserine or thiazolidine derivatives thereof. This augmented expression surprisingly results in increased secretion of amino acids or amino acid derivatives which are formed intracellularly, such as L-cysteine, L-cystine, N-acetylserine and thiazolidine derivatives thereof, out of the cell. This results in substantially higher yields of these products being achieved during fermentation.

The invention consequently also relates to a process for preparing L-cysteine, L-cystine, N-acetylserine or thiazolidine derivatives thereof which comprises employing a microorganism, which overexpresses efflux genes, in the fermentation in a manner known per se.

The process according to the invention for the fermentative preparation of L-cysteine, L-cystine, N-acetylserine or thiazolidine derivatives possesses several advantages:

Only thiazolidine diastereomers which possess the R configuration at the C4 carbon atom are formed. This is because as a result of the enzymic equipment of the cell, L-cysteine is formed stereoselectively, with this L-cysteine then being able to react with the particular ketone or aldehyde which is available. This will then yield the thiazolidine diastereomers exclusively.

Conventional chemical and biological methods and techniques can be used to obtain L-cysteine from the thiazolidines which possess the R configuration at the C4 carbon atom simply by displacing the equilibrium in the direction of the starting compounds.

Furthermore, it is a surprising and advantageous discovery that in fermentation, one can prepare L-cysteine from a thiazolidine derivative which has been formed intracellularly. A more detailed investigation of this surprising discovery led to the finding that thiazolidine is substantially less toxic for the cell than is L-cysteine.

The present invention also relates to a process for preparing L-cysteine, which comprises reacting L-cysteine, which is formed intracellularly by a microorganism, intracellularly, in the microorganism, with a ketone or aldehyde which is present intracellularly in this microorganism, to produce a thiazolidine derivative. Then this thiazolidine derivative is secreted out of the microorganism using a protein which is directly suitable for secreting antibiotics, or other substances which are toxic for the microorganism, out of the cell. Where appropriate after having separated off the thiazolidine derivative, L-cysteine is obtained by displacing the reaction equilibrium between L-cysteine and the thiazolidine derivative in the direction of L-cysteine.

One embodiment for forming a thiazolidine derivative intracellularly is to react the L-cysteine with a ketone or aldehyde which is in each case present intracellularly. Many ketones and aldehydes which are suitable for the condensation are known in the metabolic pathways of organisms. In bacterial metabolic pathways, these ketones and aldehydes include, for example, pyruvate, oxaloacetate, α-ketoglutarate and glyoxylate. L-Cysteine preferably reacts with pyruvate or glyoxylate.

Accordingly, for the thiazolidine derivatives which are formed in the process according to the invention, at least one radical $R_1$ or $R_2$ in the above reaction sequence preferably denotes a carboxyl group. Particular preference is where $R_1$ represents COOH and $R_2$ represents $CH_3$ in formula I.

The starting compounds for the condensation which gives rise to the thiazolidine derivative can both be formed by the microorganism. Alternatively, only one starting compound is formed by the microorganism and the second starting compound is added during the fermentation.

In a preferred embodiment of the invention, both of the starting compounds for the condensation giving rise to the thiazolidine derivative are formed by the microorganism.

Hydroxylamine or 2,4-dinitrophenylhydrazine can, inter alia, be used as derivatizing agents for the purpose of derivatizing pyruvate, which can thereby be removed from the equilibrium.

In the process according to the invention, the thiazolidine derivative (and the corresponding hemithioketal) can advantageously be prepared from simple and inexpensive sources of carbon, nitrogen and sulfur.

In the process according to the invention, the C sources, such as glucose, lactose, fructose, starch and the like, N sources, such as ammonium or protein hydrolyzates and the like, and S sources, such as sulfide, sulfite, sulfate, thiosulfate or dithionite, which are customary in fermentation can be used in the fermentation.

The thiazolidine derivatives which are obtained by fermentation may be used for other purposes as well as obtaining cysteine. Many application possibilities are known which can make use of the thiazolidine derivatives which have been prepared by fermentation, and which have the R configuration at the C4 carbon atom, as a starting point (building block) for more extensive syntheses.

BRIEF DESCRIPTION OF THE DRAWINGS

Other objects and features of the present invention will become apparent from the following detailed description considered in connection with the accompanying drawings and examples which disclose several embodiments of the present invention. It should be understood, however, that the drawings and examples are designed for the purpose of illustration only and not as a definition of the limits of the invention.

In the drawings, wherein similar reference characters denote similar elements throughout the several views:

FIG. 6 shows (SEQ ID NO: 5);

FIG. 7 shows (SEQ ID NO: 6);

FIG. 8 shows (SEQ ID NO: 7);

FIG. 9 shows (SEQ ID NO: 8);

FIG. 10 shows (SEQ ID NO: 9);

FIG. 11 shows (SEQ ID NO: 10);

FIG. 12 shows (SEQ ID NO: 11); and

FIG. 13 shows (SEQ ID NO: 12).

DETAILED DESCRIPTION OF PREFERRED EMBODIMENTS

Figure 1:
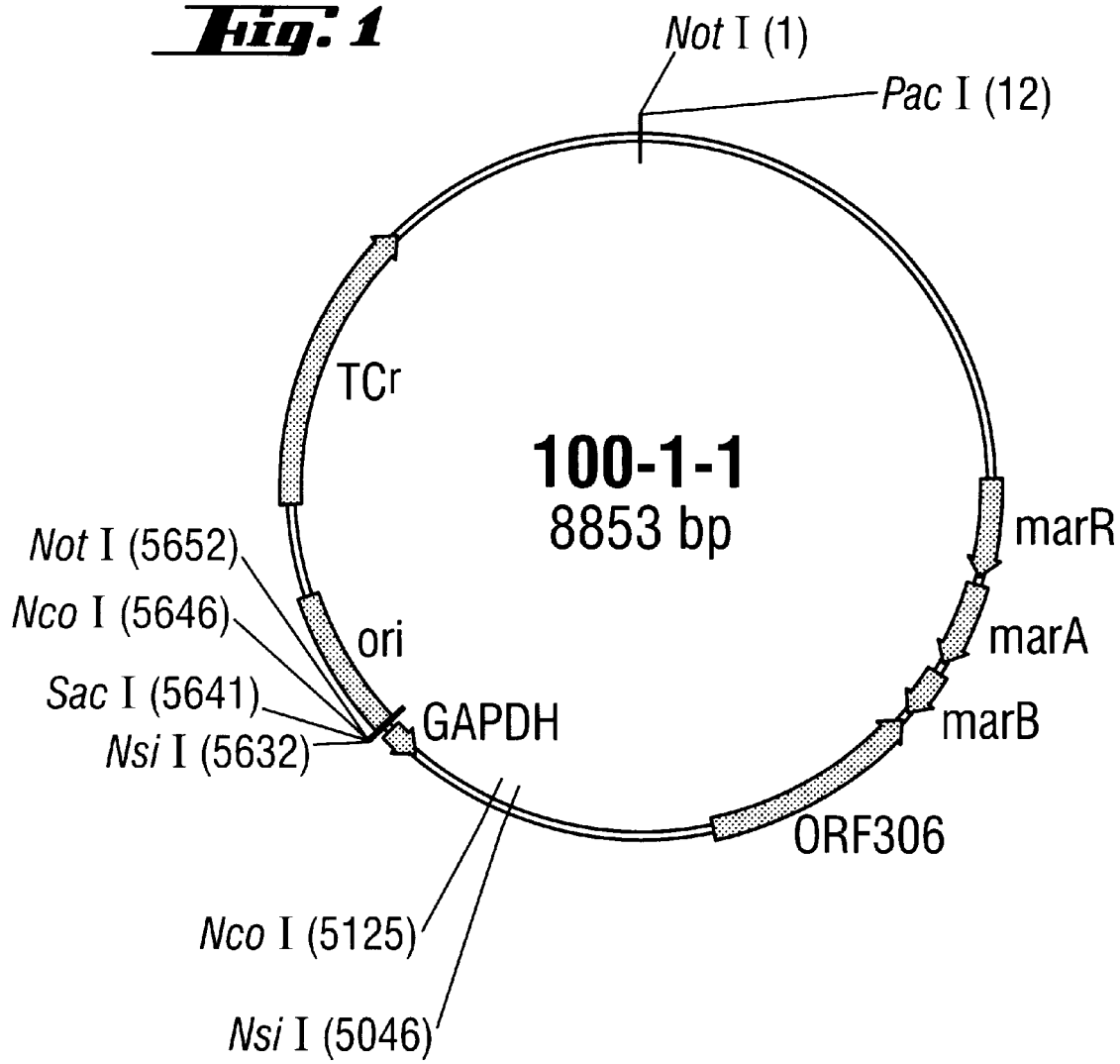
FIG. 1 shows a map of the plasmid 100-1-1.

In the Examples, it is only possible to quantitatively determine the thiazolidine derivative/hemithioketal indirectly. In the examples, these compounds were determined by determining cysteine using the method of Gaitonde, M. K. (1967), Biochem. J. 104, 627–633. Derivatizing the cysteine with ninhydrin in strongly acid conditions removes it from the equilibrium. This results in the hemithioketal reacting subsequently, followed finally by the thiazolidine derivative. After about 10 minutes at 100° C., all the thiazolidine derivative and the affiliated hemithioketal have been converted into the cysteine-ninhydrin derivative, which can then be quantified at 560 nm. In this method, the free cysteine is included in the determination.

The quantity of free SH groups, and consequently of free cysteine alone was determined by means of the test described by Sang-Han Lee et al., Biochemical and Biophysical Research Communications, Vol. 213, No. 3 (1995), pages 837ff, using 5,5'-dithiobis-2-nitrobenzoic acid (DTNB).

When free L-cysteine is formed, it is oxidized to L-cystine during the fermentation by the atmospheric oxygen which is introduced. Cystine is only sparingly soluble in aqueous medium at pH 7.0 and precipitates as a white pellet. When an insoluble cysteine pellet formed, it was dissolved in half-concentrated HCl and likewise measured in the above-mentioned test under reducing conditions obtained by using dithiothreitol (DTT).

In Example 3, the quantities of "total cysteine" which were measured in the supernatant using the Gaitonde test are given as the fermentation results. In this context, the "total cysteine" consists, in particular, of 2-methylthiazolidine-2, 4-dicarboxylic acid, the affiliated hemithioketal, free L-cysteine and dissolved cystine. Precipitated cystine was quantified and indicated separately.

The facility with which the 2-methyl-thiazolidine-2,4-dicarboxylic acid, which is produced in the embodiment of the present invention, can be precipitated using doubly charged metal ions can be exploited when detecting the formation of this derivative. The derivative has only previously been reported to be precipitatable with zinc acetate (Schubert et al., see above literature reference). However, it is also possible to precipitate it with other doubly charged metal ions such as magnesium, iron, copper, zinc, manganese, cobalt and the like. The precipitation, and subsequent identification, of the thiazolidine product formed is described in Example 4. This example also shows that 2-methylthiazolidine-2,4-dicarboxylic acid is the main product after a fermentation period of 24 hours. The ease with which this fermentation product can be precipitated is both helpful when analyzing it and useful when purifying it.

EXAMPLE 1

Amplification of the Alleles by Means of PCR

A. Amplification of the cysE Alleles

The cysE alleles, i.e. cysEIV and cysEX, which are used below are described in DE 19539952 Example 2/10.

The mutatations which are mentioned in that document can be prepared using site-directed mutagenesis. Kits for carrying out the mutagenesis can be obtained commercially, for example from Stratagene (Stratagene GmbH, PO Box 105466, D-69044 Heidelberg) under the trademarks EXSITE® or CHAMELONE®.

After the site-directed mutagenesis had been carried out, the resulting alleles were amplified from the relevent DNA by means of the polymerase chain reaction (PCR) (Saiki et al. 1988, Science 239: 487–491) using the following primers.

cysE-fw: (SEQ ID NO: 5). This sequence is shown in FIG. 6.

cysE-rev: (SEQ ID NO: 6). This sequence is shown in FIG. 7.

The PCR experiments were carried out in 30 cycles in the presence of 200 $\mu$M of deoxynucleotide triphosphates (DATP, dCTP, dGTP, dTTP), 1 $\mu$M each of the corresponding oligonucleotides, 100 ng of template DNA containing the particular cysE allele, $\frac{1}{10}$ 10 times reaction buffer (100 mM, KCl, 100 mM $(NH_4)_2SO_4$, 200 mM tris-HCl (pH 8.8), 20 mM $MgSO_4$, 1% Triton X-100 and 1000 $\mu$g/ml BSA) and 2.5 units of a heat-stable, recombinant Pfu DNA polymerase (Stratagene) in a Thermocycler (Gene-ATAQ-Controller, Pharmacia) and using the following conditions: 94° C. for 1 min, 60° C. for 1 min and 72° C. for 3 min.

The amplification product was hydrolyzed with SacI and NsiI (both from Boehringer Mannheim GmbH) under the conditions stipulated by the manufacturer, separated in 1% agarose gel and then isolated from the agarose gel as a fragment of approximately 1.0 kb in size using the Geneclean method (Geneclean kit BI0101 P.O. Box 2284 La Jolla, Calif., 92038-2284) in accordance with the manufacturer's instructions. Until further use, the fragment was stored at −20° C.

B. Amplification of the Mar Locus

The *Escherichia coli* mar locus was amplified by means of PCR. The method for isolating the amplificates is the same as that described in Example 1 Section A. The chromosomal DNA from *Escherichia coli* W3110 (ATCC 27325) was used as the template DNA. Plasmid 100-1-1 (DSM 11545) can also be used as the template DNA. The cells were lysed, and the chromosomal DNA was purified, in accordance with the protocol described in Ausubel et al., 1987, 2.4.1–2.4.2, Current Protocols in Molecular Biology, Greene Publishing Associates and Wiley-Interscience. The following primers were used for amplifying the mar locus:

mar-fw: (SEQ ID NO: 7). This sequence is shown in FIG. 8.

mar-rev: (SEQ ID NO: 8). This sequence is shown in FIG. 9.

Amplification of the mar locus gave rise to a fragment which was approximately 3 kb in size and which was purified as described in Example 1 Section A. The subsequent restriction digestion was carried out using the enzymes AscI and PacI (both from New England Biolabs GmbH, P.O. Box 2750, D-65820 Schwalbach/Taunus) in accordance with the instructions, and using the buffers, of the manufacturer. After the fragment had been purified by agarose gel electrophoresis, it was stored at –20° C.

C. Amplification of the ORF306 DNA

The DNA encoding ORF306 was amplified by PCR as described in Example 1 Section A. The chromosomal DNA which was isolated from *E. coli* W3110 (ATCC 27325) in Example 1 Section B was used as the template DNA. Plasmid 100-1-1 (DSM 11545) can also be used as the template DNA. The following primers were used:

ORF306-fw: (SEQ ID NO: 9). This sequence is shown in FIG. 10.

ORF306-rev: (SEQ ID NO: 10). This sequence is shown in FIG. 11.

The amplified DNA fragment is about 1.05 kb in size and was purified by agarose gel electrophoresis, as described. Subsequent restriction digestion with the enzymes AsnI (Boehringer Mannheim) and PacI (New England Biolabs) yielded the desired DNA fragment after the enzymes had been removed. This fragment was stored at –20° C. until use.

D. Amplification of the DNA Fragment Encoding the GAPDH Promoter.

The promoter of the glyceraldehyde-3-phosphate dehydrogenase gene was used in order to obtain effective transcription of ORF306. This desired DNA fragment was likewise obtained by means of PCR. The chromosomal DNA from *Escherichia coli* W3110 (ATCC 27325) was once again used as the template DNA. Plasmid 100-1-1 can also be employed as the template DNA. The following primers were used:

GAPDH-fw (SEQ ID NO: 11). This sequence is shown in FIG. 12.

GAPDH-rev: (SEQ ID NO: 12). This sequence is shown in FIG. 13.

The resulting DNA fragment, of about 0.3 kb in size, was isolated by agarose gel electrophoresis and purified as described in Ex. 1 Section A. Subsequent restriction digestion with the enzymes MluI and PacI yielded the desired DNA fragment. After the restriction enzymes had been removed, the DNA was stored at –20° C.

EXAMPLE 2

Construction of the Plasmids According to the Invention

Plasmid pACYC184 was used as the basic plasmid for constructing the plasmids of the invention. This plasmid was modified as described in DE 19539952 and deposited, as plasmid pACYC184-LH, in the Deutsche Sammlung fur Mikroorganismen in Braunschweig under deposition number DSM 10172.

Figure 2:
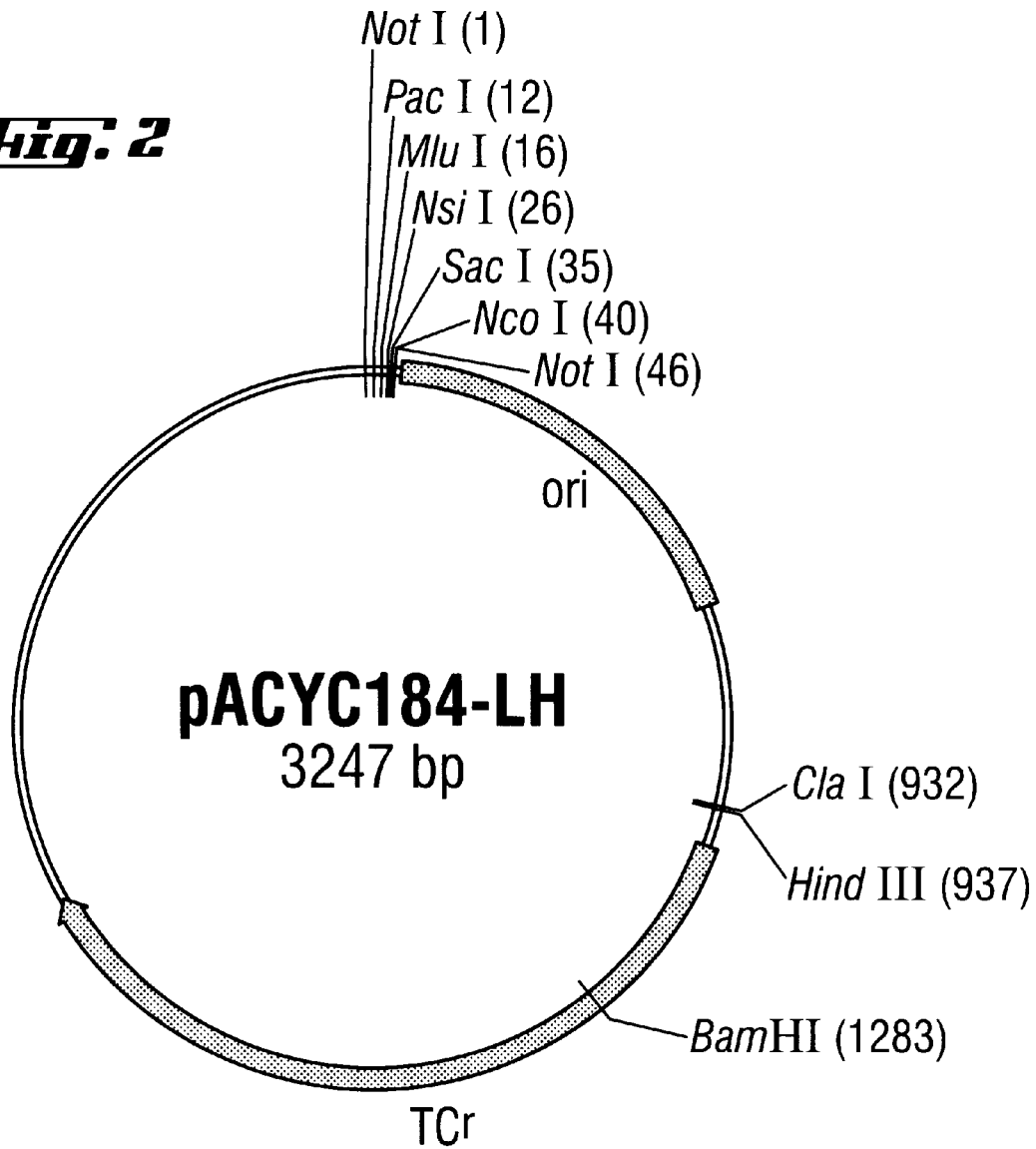
FIG. 2 shows a restriction map and functional map of plasmid pACYC184-LH.

FIG. 2 shows a restriction map and functional map of plasmid pACYCCC184-LH. Plasmid pACYC184-LH carries a poly-linker. This polylinker possesses the following restriction cleavage sites:

NotI-NcoI-Sac-NsiI-MluI-PacI-NotI

The DNA fragments which were obtained in Example 1 by means of PCR and subsequent restriction digestion were ligated into this linker.

A. Construction of the control plasmids pACYC184/cysEIV and pACYC184/cysEX

The preparation of plasmid pACYCl184/cysEIV and pACYC184/cysEX is described in DE 19539952 EX. 3 and is briefly summarized below:

Approximately 1 µg of plasmid pACYC184-LH (DSM 10172) was digested with the restriction enzymes SacI and NsiI in accordance with the manufacturer's (Boehringer Mannheim) instructions. The digested DNA was then purified by agarose gel electrophoresis in order to remove the enzymes, as has previously been described. The DNA fragments which were obtained in Example 1 Section A, and which encoded the respective cysE alleles, were then mixed in equimolar proportions with the SacI- and NsiI-digested plasmid pACYC184-LH; 1 µl of T4 DNA ligase and 2 µl of 10 times ligase buffer (both from Boehringer Mannheim) were then added to this mixture, which was made up to a total volume of 20 µl with sterile, double-distilled $H_2O$. The mixture was incubated at 4° C. overnight and used to transform *Escherichia coli* W3110 (ATCC 27325). The transformation method which is described below was used in all the transformations mentioned in the examples.

*E. coli* W3110 was transformed by means of electroporation. For this, 500 ml of LB medium (10 g of tryptone, 5 g of yeast extract and 5 g of NaCl) in a 1 l Erlenmeyer flask were inoculated with 1% (V/V) of an overnight culture in the same medium. After incubating in an orbital shaker at 37° C. to an optical density of 0.5-0.6 at 600 nm, the cells were harvested by centrifuging in a sterile container at 4° C. All subsequent steps were then carried out on ice and while maintaining sterile conditions. The cell pellet was next washed twice with 500 ml of ice-cold, sterile, double-distilled $H_2O$, and finally resuspended in 30 ml of 10% (V/V) sterile glycerol. After a further centrifugation, the cell pellet was taken up in 500 µl of 10% (V/V) glycerol and stored at –80° C. in 200 µl aliquots. For the transformation, the cells were thawed on ice, after which about 10–100 ng of DNA were added to them and the mixture was introduced into a sterile electro-poration cuvette (BioRad). The cuvette was placed in the Gene Pulser (BioRad), and electroporation was carried out at a voltage of 2500 volts, a parallel resistance of 200 ohms and a capacitance of 25 µF. The cells were then resuspended in 1 ml of SOC medium (casein peptone, 20.0 g/l, yeast extract, 5.0 g/l, NaCl, 0.58 g/l, KCl, 0.19 g/l, $MgCl_2$, 2.03 g/l, $MgSO_4$, 2.46 g/l, glucose, 3.60 g/l, pH=7.0) and shaken at 37° C. for 1 hour. After that, the cells were diluted appropriately and plated on LB agar plates (10 g/l tryptone, 5 g/l yeast extract, 5 g/l NaCl, 15 g/l agar, pH=7.2), after which the plates were incubated at 37° C. overnight until individual colonies became visible.

The desired transformants were identified by restriction analysis after the plasmids had been isolated using a QIAprep Spin plasmid kit (Qiagen GmbH, Max-Volmerstrasse 4, D-40724 Hilden). They were used in Example 3 as controls in the fermentation.

Figure 3:
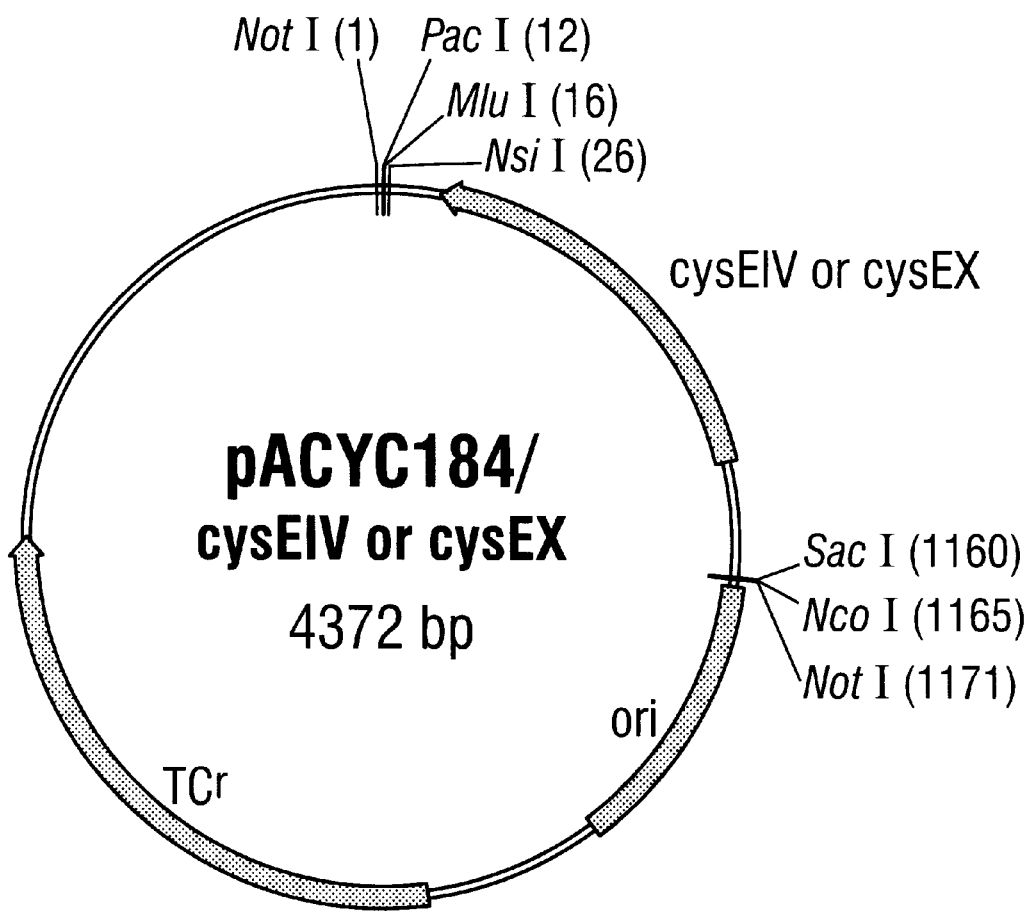
FIG. 3 shows a map of plasmids pACYC184/cysEIV and pACYC184/cysEX.

Plasmids pACYC184/cysEIV and pACYC184/cysEX are depicted in FIG. 3.

B. Construction of Plasmids pACYC184/cysEIV-mar and pACYC184/cysEX-mar.

Figure 4:
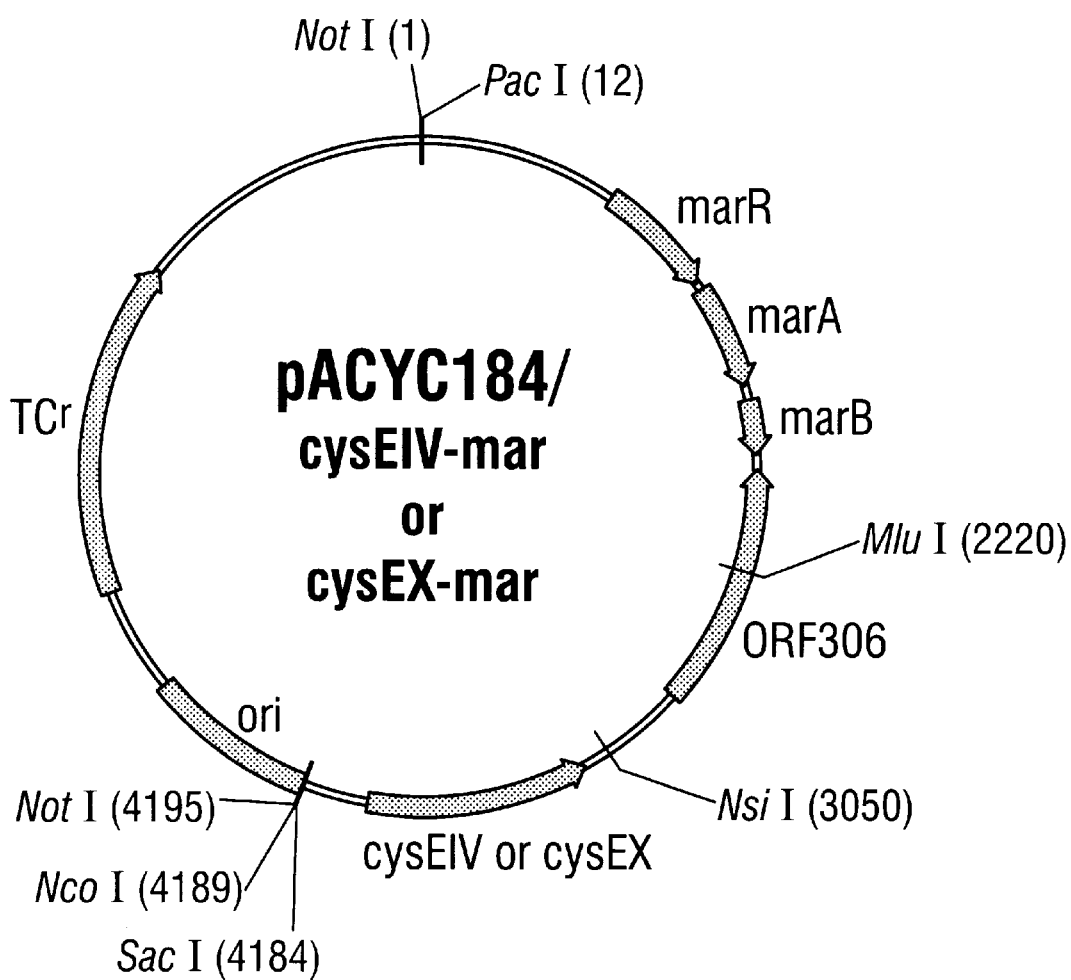
FIG. 4 shows a restriction map and a functional map of plasmids pACYC184/cysEIV-mar and pACYC184/cysEX-mar.

In each case, 1 μg of the plasmids pACYC184/cysEIV and pACYC184/cysEX, which were constructed in Example 2 Section A, was digested consecutively with the restriction enzymes MluI (Boehringer) and PacI (New England Biolabs) in accordance with the manufacturers' instructions. After this restriction digestion, the DNA was isolated by agarose gel electrophoresis and purified as described in Example 1 Section A. Approximately 20 ng of the MluI/PacI-digested vectors pACYC184/cysEIV or pACYC184/cysEX were in each case mixed with 200 ng of the DNA fragment prepared in Example 1 Section A, 1 μl of T4 DNA ligase (Boehringer Mannheim) and 2 μl of 10 times ligase buffer (Boehringer Mannheim) and the requisite quantity of sterile, double-distilled $H_2O$ in a final volume of 20 μl. After incubating at 4° C. overnight, the two DNA mixtures were used to transform Escherichia coli W3110 (ATCC 27325). After plasmids had been isolated using the QIAprep Spin plasmid kit (Qiagen GmbH) and subjected to a restriction analysis, the desired transformants were isolated and employed in the fermentation, as described in Example 3. FIG. 4 shows restriction maps and functional maps of plasmids pACYC184/cysEIV-mar and pACYC184/cysEX-mar.

C. Construction of Plasmids pACYC184/cysEIV-GAPDH and pACYC184/cysEX-GAPDH

The plasmids pACYC184/cysEIV and pACYC184/cysEX, which were constructed in Example 2 Section A, were in each case digested with the restriction enzymes MluI (Boehringer Mannheim) and PacI (New England Biolabs) in accordance with the manufacturers' instructions.

After the plasmids which had been treated in this way had been purified, two ligations were in each case started, as described in Example 2 Section B, using the DNA fragment which was prepared in Example 1 Section D.

After having been incubated at 4° C. overnight, the ligation mixtures were transformed into E. coli W3110. The correct transformants were identified, after the plasmid DNA had been isolated, by analysis using suitable restriction enzymes.

Plasmids pACYC184/cysEIV-GAPDH and pACYC184/cysEX-GAPDH were used as the starting materials for constructing the plasmids pACYC184/cysEIV-GAPDH-ORF306 and pACYC184/cysEX-GAPDH-ORF306, as described in Section D below.

D. Construction of Plasmids pACYC184/cysEIV-GAPDH-ORF306 and pACYC184/cysEX-GAPDH-ORF306

The plasmids prepared in Section C were digested with NdeI (Boehringer Mannheim) and PacI (New England Biolabs) in accordance with the manufacturers' instructions. After the plasmid DNA had been purified, two ligations were started using the DNA fragment from Example 1 Section C which had been cut with AsnI-PacI and which encoded ORF306.

After having been incubated at 4° C. overnight, the DNA mixtures were in each case transformed into E. coli W3110, and the transformed bacteria were plated out on LB plates. Once the single colonies had appeared, they were tested for correctness by isolating their plasmids and subjecting them to restriction digestion.

Figure 5:
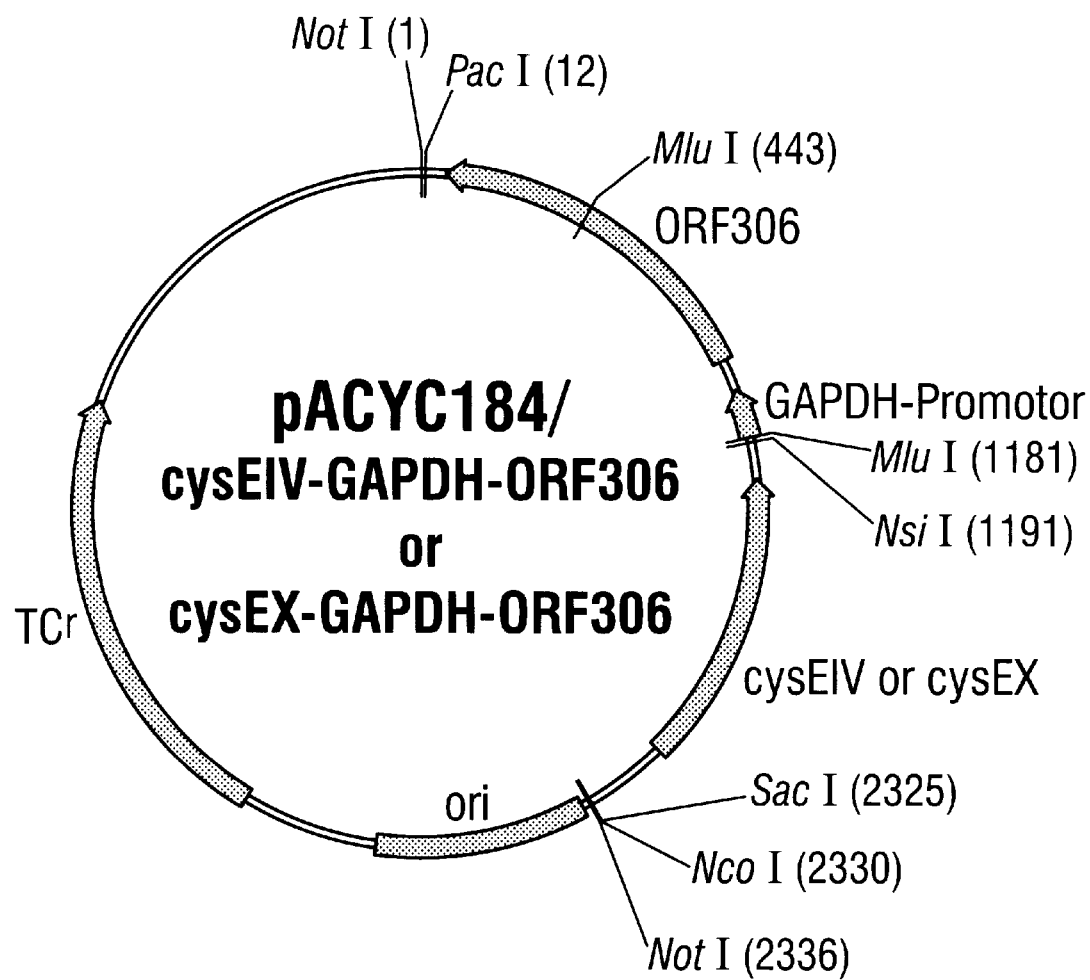
FIG. 5 shows a restriction map and a functional map of plasmids pACYC184-cysEIV-GAPDH-ORF306 and pACYC184/CYSEX-GAPDH-ORF306.

FIG. 5 shows restriction maps and functional maps of plasmids pACYC184-cysEIV-GAPDH-ORF306 and pACYC184/CYSEX-GAPDH-ORF306.

EXAMPLE 3

Comparison of the yields, in fermentation, of the constructs according to the invention-and of known constructs.

All the plasmids which were compared in the fermentation were fermented in E. coli W3110. This thereby guarantees that the yield increases which were in each case observed only resulted from the novel use of the genes.

20 ml of LB medium containing 15 mg/l tetracycline were inoculated with the respective E. coli construct in an Erlenmeyer flask (100 ml). After having been incubated for 7 hours in a shaker incubator (150 rpm, 30° C.), the respective preliminary cultures were transferred to 100 ml of SM1 medium (12 g/l $K_2HPO_4$, 3 g/l $KH_2PO_4$, 5 g/l $(NH_4)_2SO_4$, 0.3 g/l $MgSO_4\times7$ $H_2O$, 0.015 g/l $CaCl_2\times2$ $H_2O$, 0.002 g/l $FeSO_4\times7$ $H_2O$, 1 g/l $Na_3$citrate$\times2$ $H_2O$, 0.1 g/l NaCl, 1 ml/l of trace element solution, consisting of 0.15 g/l $Na_2MoO_4\times2H_2O$, 2.5 g/l $H_3BO_3$, 0.7 g/l $CoCl_2\times6$ $H_2O$, 0.25 g/l $CuSO_4\times5$ $H_2O$, 1.6 g/l $MnCl_2\times4$ $H_2O$, 0.3 g/l $ZnSO_4\times7$ $H_2O$), which was supplemented with 5 g/l glucose, 5 mg/l vitamin B1 and 15 mg/l tetracycline. The cultures were shaken at 150 rpm and 30° C. for 17 h in Erlenmeyer flasks (1 l). After this incubation, the optical density at 600 nm ($OD_{600}$) was between 3 and 5.

The fermentation was carried out in BIOSTAT M Braun-Melsungen fermenters. A culture vessel having a total volume of 2 l was used. The fermentation medium contains 15 g/l glucose, 10 g/l tryptone (Difco), 5 g/l yeast extract (Difco), 5 g/l $(NH_4)_2SO_4$, 1.5 g/l $KH_2PO_4$, 0.5 g/l NaCl, 0.3 g/l $MgSO_4\times7$ $H_2O$, 0.015 g/l $CaCl_2\times2$ $H_2O$, 0.075 g/l $FeSO_4\times7$ $H_2O$, 1 g/l $Na_3$citrate$\times2$ $H_2O$ and 1 ml of trace element solution (see above), 0.005 g/l vitamin B1 and 15 mg/l tetracycline. The pH in the fermenter was initially adjusted to 7.0 by pumping in a 25% solution of $NH_4OH$. During the fermentation, the pH was maintained at a value of 7.0 by means of automatic correction with 25% $NH_4OH$. For the inoculation, 100 ml of preliminary culture were pumped into the fermenter vessel. The starting volume was about 1 l. The cultures were initially stirred at 200 rpm and gassed with 1.5 vvm of compressed air which had been sterilized by being passed through a sterilization filter. The atmospheric oxygen saturation during the fermentation was adjusted to 50%. This was controlled automatically by way of the stirring rate. The fermentation was carried out at a temperature of 30° C. After the fermentation had been in progress for 2 h, a sterile 30% stock solution of Na-thiosulfate$\times5$ $H_2O$ was fed in at a rate of 3 ml per hour. After an $OD_{600}$ of 10 had been reached, a sterile 56% stock solution of glucose was metered in at a rate of about 8–14 ml per hour. The glucose content was determined enzymically using a glucose analyzer from YSI. During the fermentation, the glucose concentration was adjusted to between 10 and 20 g/l by feeding it in continuously. The total content of cysteine in the medium was determined calorimetrically in accordance with Gaitonde, M. K. (1967), Biochem. J. 104, 627–633 from the cell-free supernatant of the sample. In this context, it is to be noted that the cysteine remaining in solution during the fermentation was present in the main as the thiazolidine derivative but was nevertheless recorded by the test. If the ketone or aldehyde (in this case pyruvate) is no longer available in sufficient quantities for converting the cysteine which is formed into the thiazolidine derivative, free L-cysteine is then formed, which cysteine is also likewise recorded by the test. When free L-cysteine is formed, it is slowly oxidized to L-cystine during the fermentation by the atmospheric oxygen which is introduced. Cystine is only sparingly soluble in aqueous medium at pH 7.0 and precipitates out as a white pellet. When an insoluble cystine pellet formed, it was dissolved, after the supernatant had been separated off from a withdrawn sample, and after centrifugation, in half-concentrated HCl and likewise measured in the abovementioned test under reducing conditions (DTT).

Under these conditions, the yields shown in Tables 1 and 2 were achieved after fermentation periods of 24 hours and 48 hours, respectively. These tables provide clear evidence that the genes employed in accordance with the invention, i.e. the E coli mar-locus and, in particular, the segment encoding ORF306, markedly increase the yields of cysteine and/or thiazolidine derivative (total cysteine). The formation of a cystine precipitate is recorded separately in the tables.

TABLE 1

Yields of total cysteine using the cysEIV allele

| Fermentation time | Yields of total cysteine (g/l) using the following plasmid constructs | | |
|---|---|---|---|
| | pACYC184/ cysEIV | pACYC184/ cysEIV-mar | pACYC184/cysEIV-GAPDH-ORF306 |
| 24 hours | 1 | 3.8 | 3.8 |
| 48 hours | 1.6 | 5 | 3.2 ± 6.3* |

*Quantity of cystine, in grams per liter, which is present as a pellet.

TABLE 2

Yields of total cysteine using the cysEX allele

| Fermentation time | Yields of total cysteine (g/l) using the following plasmid constructs | | |
|---|---|---|---|
| | pACYC184/ cysEX | pACYC184/ cysEX-mar | pACYC184/cysEX-GAPDH-ORF306 |
| 24 hours | 4.9 | 5.9 | 12.8 |
| 48 hours | 6.8 | 11.4 | 7.2 ± 12.0* |

*Quantity of cystine, in grams per liter, which is present as a pellet.

EXAMPLE 4

Demonstration of the Formation of 2-methylthiazolidine-2,4-dicarboxylic acid

The construct E. coli W3110 x pACYC184/cysEX-GAPDH-ORF306 was fermented as described in Example 3 in order to demonstrate that 2-methylthiazolidine-2,4-dicarboxylic acid was formed as the main product of the fermentation described in Example 3.

After 24 hours, the fermentation supernatant was separated from the cells by centrifugation. The cysteine measurement which has been described gave a value of 12.8 g for the total cysteine in the supernatant. MgSO$_4$ was then added to the fermentation supernatant to give a final concentration of 0.3 M. A white precipitate formed after this supernatant had been incubated overnight at 4° C. with stirring. This precipitate was the sparingly soluble magnesium salt of 2-methylthiazolidine-2,4-dicarboxylic acid.

After this precipitate had been separated off by centrifugation, the residual quantity of cysteine in the supernatant was measured to be only 2.5 g/l.

The precipitate was dissolved in half-concentrated HCl and likewise subjected to a cysteine test. In this case, the cysteine concentration was found to be 9.5 g/l. After the precipitate, dissolved in D$_2$O+HCl, had been investigated by $^1$H NMR and $^{13}$C NMR, it was identified against a reference substance (M. P. Schubert, J. Biol. Chem. 121, 539–548 (1937) as being 2-methylthiazolidine-2,4-dicarboxylic acid.

EXAMPLE 5

Different Toxicities of L-cysteine and 2-methylthiazolidine-2,4(R)-dicarboxylic acid For this experiment, 2-methylthiazolidine-2,4(R)-dicarboxylic acid was synthesized from L-cysteine and pyruvate using the method of Schubert (M. P. Schubert, J. Biol. Chem. 121, 539–548 (1937)). An overnight culture of E. coli W3110 in LB medium was inoculated into 20 ml of SM1 medium (see Example 3) which was supplemented with 10 g/l of glucose, 10% LB medium, 5 mg/l vitamin B1, 15 mg/l tetracycline and in each case appropriate quantities of L-cysteine or 2-methylthiazolidine-2,4(R)-dicarboxylic acid. Following a 7-hour incubation at 37° C., no further growth was found in the L-cysteine-containing medium at concentrations of 1 mM and above, whereas growth could be observed in the medium containing 2-methylthiazolidine-2, 4(R)-dicarboxylic acid up to a concentration of 50 mM. It was not possible to incubate for longer periods because of the ready oxidizability of the cysteine. Consequently, L-cysteine is markedly more toxic for E. coli than is 2-methylthiazolidine-2,4(R)-dicarboxylic acid. 2-Methylthiazolidine-2,4(R)-dicarboxylic acid is therefore much more suitable for obtaining L-cysteine by means of fermentative methods even if, in this case, a chemical step is still required in order to liberate the L-cysteine.

EXAMPLE 6

Augmented Formation of N-acetyl-L-serine

N-Acetyl-L-serine is formed from O-acetyl-L-serine by spontaneous rearrangement. This O-acetyl-L-serine is the immediate precursor of L-cysteine in the bacterial biosynthetic pathway. Consequently, the end product of such a fermentation is N-acetyl-L-serine when incorporation of sulfur into O-acetyl-L-serine is either inadequate or absent. When there is no sulfur supply, the genes according to the invention also increase the yield of this fermentation product.

The fermentation described in Example 3 was carried out without feeding thiosulfate. The constructs employed, which were intended to demonstrate the efficacy of the genes they contained, in particular of ORF306, were pACYC184/cysEX and pACYC184/cysEX-GAPDH-ORF306.

As the results in Table 3 show, the genes according to the invention, in particular ORF306, markedly increase the yield of N-acetyl-L-serine in the fermentation.

TABLE 3

Yields of N-acetyl-L-serine after 24 h of fermentation

| Construct | N-Acetyl-L-serine (g/l) |
|---|---|
| pACYC184/cysEX | 7.6 |
| pACYC184/cysEX-GAPDH-ORF306 | 15.9 |

Yields of N-acetyl-L-serine of more than 30 g/l can be achieved when more strongly feedback-resistant cysE alleles (for example cysEXIV, cysEXI and cysEXXII from DE 19539952) are used in combination with the genes according to the invention.

While several embodiments of the present invention have been shown and described, it is to be understood that many changes and modifications may be made thereunto without departing from the spirit and scope of the invention as defined in the appended claims.

What is claimed is:

1. A microorganism strain which is useful for the fermentative preparation of an increased yield of a substance selected from the group consisting of L-cysteine, L-cystine, N-acetylserine, a thiazolidine derivative and the mixtures thereof, said strain overexpressing at least one gene which encodes a protein which is directly suitable for secreting an antibiotic, or other substances which are toxic for the microorganism, out of a cell;

said microorganism strain being selected from the group consisting of Bacillus, Corynebacteria, Streptomyces, and E. coli and said microorganism strain producing L-cysteine, and said microorganism strain having a deregulated metabolism of L-cysteine, which results in a sustained increase in L-cysteine production;

such that an increased yield of L-cysteine or said other substances result.

2. A microorganism strain as claimed in claim 1 wherein said at least one gene is selected from the group consisting of mar locus, emr locus, acr locus, cmr locus, mex genes, bmr gene and qacA gene and is overexpressed as a gene which encodes a protein which is directly suitable for secreting antibiotics, and other substances which are toxic for the microorganism, out of the cell.

3. A microorganism strain as claimed in claim 1 wherein said at least one gene encodes a protein which comprises a sequence selected from the group consisting of (SEQ ID NO: 1) and a sequence which has greater than 50% sequence homology with (SEQ ID NO: 1), and is overexpressed as a gene which encodes a protein which is directly suitable for secreting antibiotics, and other substances which are toxic for the microorganism, out of the cell.

4. A gene encoding a protein which comprises a sequence selected from the group of (SEQ ID NO: 1) and a sequence which has greater than 50% sequence homology with (SEQ ID NO: 1).

5. A gene which encodes a protein comprising a sequence selected from the group consisting of (SEQ ID NO:2) and a sequence which has greater than 90% sequence homology with (SEQ ID NO:2).

6. A protein which comprises a sequence selected from the group consisting of (SEQ ID NO: 1) and a sequence which has greater than 50% sequence homology with (SEQ ID NO: 1).

7. A plasmid which contains at least one gene as claimed in claim 4.

8. A plasmid which contains at least one gene as claimed in claim 5.

9. A process for preparing a substance selected from the group consisting of L-cysteine, L-cystine, N-acetylserine and thiazolidine derivatives thereof, comprising
employing a microorganism strain as claimed in claim 1 in fermentation; and
producing an increased yield of said substance.

10. A process for preparing a substance selected from the group consisting of L-cysteine, L-cystine, N-acetylserine and thiazolidine derivatives thereof, comprising
employing a microorganism strain as claimed in claim 2 in fermentation; and
producing an increased yield of said substance.

11. A process for preparing a substance selected from the group consisting of L-cysteine, L-cystine, N-acetylserine and thiazolidine derivatives thereof, comprising
employing a microorganism strain as claimed in claim 3 in fermentation; and
producing an increased yield of said substance.

12. In a method for the augmented expression of amino acids, or amino acid derivatives selected from the group consisting of L-cysteine, L-cystine, N-acetylserine and thiazolidine derivatives thereof, the improvement which comprises,
expressing efflux genes selected from the group consisting of mar locus, emr locus, acr locus, cmr locus, mex genes, bmr gene, and gacA gene for the augmented expression of said amino acids, or amino acid derivatives which are formed intracellularly, in fermentation; and
producing said amino acids or amino acid derivatives in fermentation.

13. A process for preparing an increased yield of L-cysteine, comprising
fermenting a microorganism strain selected from the group consisting of Bacillus, Corynebacteria, Streptomyces, and *E. coli*, and said strain Producing L-cysteine;
said strain preventing the metabolism of L-cysteine, by having a deregulated metabolism of L-cysteine, which results in a sustained increase in L-cysteine production intracellularly;
reacting L-cysteine, intracellularly, in the microorganism, with a ketone or aldehyde which is present intracellularly in the microorganism, to produce a thiazolidine derivative;
secreting said thiazolidine derivative out of the microorganism by using a protein which is directly suitable for secreting antibiotics, and other substances which are toxic for the microorganism, out of the cell; said protein comprising a sequence consisting of (SEQ ID NO:2) or (SEO ID NO:3);
separating off the thiazolidine derivative; and
obtaining L-cysteine by displacing the reaction equilibrium between L-cysteine and the thiazolidine derivative in the direction of L-cysteine.

14. A microorganism strain which is useful for the fermentative preparation of an increased yield of a substance selected from the group consisting of L-cysteine, L-cystine, N-acetylserine, a thiazolidine derivative and the mixtures thereof;
said strain overexpressing at least one gene which encodes a protein which is directly suitable for secreting an antibiotic, or other substances which are toxic for the microorganism, out of a cell;
said protein comprising a sequence consisting of (SEQ ID NO:2) or (SEQ ID NO:3);
said microorganism strain being selected from the group consisting of Bacillus, Corynebacteria, Streptomyces, and *E. coli*; said microorganism strain producing L-cysteine; and
said microorganism strain having a deregulated metabolism of L-cysteine, which results in a sustained increase in L-cysteine production;
such that an increased yield of L-cysteine or other substance results.

* * * * *